Figure 1:
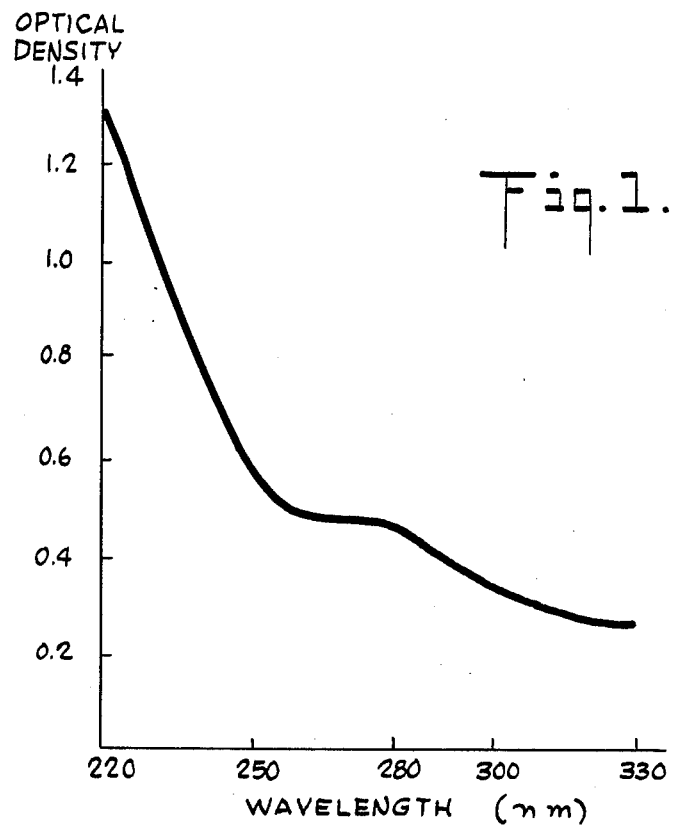

United States Patent [19]

Nakamura et al.

[11] 4,059,572

[45] Nov. 22, 1977

[54] MUCOPOLYSACCHARIDE HAVING FLOCCULATING ACTIVITY OF PROTEIN AND METHOD FOR PRODUCING THE SAME

[75] Inventors: Junji Nakamura, Tokyo; Shigeyoshi Miyashiro, Kawasaki; Yoshio Hirose, Fujisawa; Takeyoshi Awao, Kawasaki, all of Japan

[73] Assignee: Ajinomoto Co., Inc., Tokyo, Japan

[21] Appl. No.: 565,077

[22] Filed: Apr. 4, 1975

[30] Foreign Application Priority Data

Apr. 9, 1974 Japan .................................. 49-40298

[51] Int. Cl.$^2$ ............................................. C12D 13/06
[52] U.S. Cl. ............................... 260/112 R; 195/31 P
[58] Field of Search ................... 260/112 R; 195/31 P

[56] References Cited

PUBLICATIONS

Chemical Abstracts, vol. 73, No. 75671k, Kaneko, 1970.
Chem. Abs., vol. 62, No. 1047f, Usami, 1965.
Chem. Abs., vol. 63, No. 16829c, Wake, 1965.
Chem. Abs., vol. 79, No. 144885w, Yamada, 1973.
Chem. Abs., vol. 81, No. 76465y, Nakahara, Mar. 1974.
Chem. Abs., vol. 81, No. 4210p, Okuyama, Mar. 1974.

*Primary Examiner*—Paul R. Michl
*Attorney, Agent, or Firm*—Cooper, Dunham, Clark, Griffin & Moran

[57] ABSTRACT

Microorganisms of the genus Aspergillus produce mucopolysaccharides having flocculating activity for protein.

2 Claims, 2 Drawing Figures

MUCOPOLYSACCHARIDE HAVING FLOCCULATING ACTIVITY OF PROTEIN AND METHOD FOR PRODUCING THE SAME

This invention retates to a newly found mucopolysaccharide having flocculating activity of protein and method for producing the same by microorganisms.

Various materials are known to have flocculating activity of protein (flocculant), and are used for separating proteins dissolved or suspended in water. For example, persimmon tannin which is a known flocculant has been used for sedimentating lees in brewages. The other known flocculants are, for example, polyacrylamide, chitosan, calcuim ions, ferric ions, gelatin, and solium alginate. The flocculants became more important recently for precipitating proteins in waste water of food manufacturing, for separating microbial cells for the production of "single cell proteins".

A new flocculant of mucopolysaccharide has been found in a culture broth of microorganism. The mucopolysaccharide contains in the molecule amino acids, amino sugars and organic acids.

The newly found mucopolysaccharide is produced by various microorganisms as exemplified below:
  *Aspergillus sojae* AJ 7002 (FERM -P 2558)
  *Aspergillus flavus* AJ 17047 (FERM -P 2559)
  *Aspergillus ochraceus* AJ 7184 (FERM -P 2560)
  *Aspergillus tamarii* AJ 7249 (FERM -P 2561)

Microorganisms identified by FERM -P numbers are available from the Fermentation Research Institute of the Agency of Industrial Science & Technology, Chiba-shi, Chiba-ken, Japan.

When the microorganisms as above are cultured aerobically in conventional aqueous medium for 1 to 5 days preferably with adjusting pH 3 to 8 and 20° to 40° C, substantial amount of the mucopolysaccharide is accumulated in the culture medium.

The aqueous culture medium contains carbon sources, nitrogen sources, iorganic ions, and where required minor organic nutrients. Suitable carbon sources are, for example, starch, glucose, sucrose, molasses, glycerine, ethanol and acetic acid. As the nitrogen source, ammonium ions, nitrate ions, urea, proteins, amino acids and amines are preferably used. Minor organic nutrients are usually vitamines, amino acids and purines.

The mucropolysaccharide produced in the aqueous culture medium can be precipitated and recovered by adjusting a pH at 7.2 to 7.8, by addition of organic solvent such as ethanol or acetone, to the aqueous culture medium, by addition of inorganic ions such as calcium ions, magnesium ions, or aluminium ions, or by salting out method. When required, the precipitated mucopolysaccharide is purified by various known methods such as gel-filtration or ion-chromatography. The aqueous culture broth, cells and mycerium can be used for flocculating proteins as they are, since they contain enough flocculating activity for the purpose.

Figure 2:
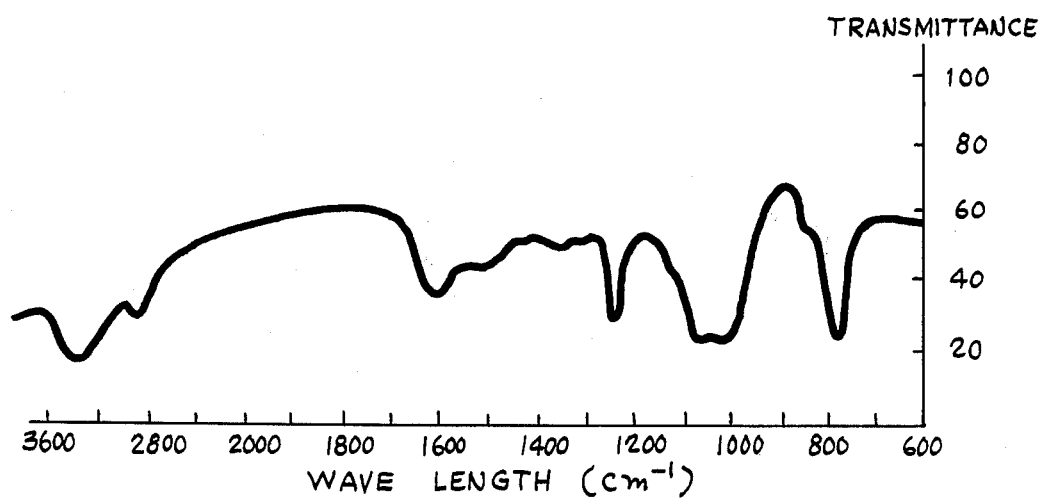

The mucopolysaccharide thus obtained has the following chemical and physical characteristics:
1. U V spectrum: FIG. 1.
2. I R spectrum: FIG. 2. (KBr)
3. Elemental analysis: Contains carbon, hydrogen, oxygen and nitrogen, but no phosphorus or sulfur.
4. Constituents:
   Proteins: 27.5%
   Amino sugars:
     glucosamine: 0.3%
     galactosamine: 20.9%
   Organic acids
     2-ketogluconic acid: 35.3%
5. Molecular weight:
   more than $2 \times 10^5$ (gel-filtration method with "Sephadex G-200")
6. Viscosity:
   400 c.p. (in 1N HCl at 22° C)
7. Contents of amino acids: Table 3
8. Stability:
   The flocculating activity is inactivated by the treatment of protease or periodic acid. When aqueous solution of the mucopolysaccharide (pH 9.0) is heated at 100° C for 20 minutes, 70% of its activities is lost, while the flocculating activity is not lost by heating at pH 7.5 and 90° C for 20 minutes
9. Amino acid contained: Table 1

Method of preparation of the mucopolysaccharide: An aqueous culture medium was prepared to contain, per deciliter, 0.1 g $KH_2PO_4$, 0.1 g $MgSO_4.7H_2O$, and 2.0g casein.

15 L of the aqueous culture medium was placed in 30 l fermentation vessel, and inoculated with Aspergillus sojae FERM -P 2558. Cultivation was carried out aerobically at 30° C for 48 hours.

Culture broth thus obtained was centrifuged to remove mycerium, and adjusted with 6N HCl at pH 7.0. The precipitates of mucopolysaccharide were separated by filtration and washed with 500 ml acetone and subsequently 300 ml chloroform-methanol mixture, and dissolved in 2 l of 1N HCl. After removing impurities by centrifuging, the solution was adjusted to pH 7.0 with 6N NaOH, whereby precipitates of the mucopolysaccharide were formed. This purification procedure was repeated twice. The resultant precipitates were washed with 200 ml of 0.005N NaOH twice and 300 ml of water once, and dissolved in 200 ml of 0.1N HCl. The solution was added with trichloroacetic acid to contain 5 g/dl in the solution, and heated at 50° C for 10 minutes, centrifuged to remove impurities, and dialyzed against 100 l water for 72 hours. Freeze-dried mucopolysaccharide (1.45 g) was separated from the dialyzed solution.

The mucopolysaccharide produced by an Aspergillus microorganism employed in this invention may differ slightly from that produced by another. All mucopolysaccharides within the scope of the invention, however, will have the foregoing chemical and physical characteristics.

The mucopolysaccharide of this invention can be applied for flocculating and sedimentating any proteins dissolved or suspended in water, and used for recovering proteins or removing proteins from waste water containing proteins. For example, yeast, bacterial cells and mycerium which are a protein can be easily sedimentated when the mucopolysaccharide is added to the solution containing those microbial cells and therefore the mucopolysaccharide can be applied for "Sincle Cell Protein" production. Waste water from which proteins are removed by the mucopolysaccharide is, for example, fermentation processing water, brewing water, and fish processing water. The mucopolysaccharide can be applied also for sedimentating lees in brewages or in refressing drinks.

EXAMPLE 1

An aqueous culture medium (50ml) containing, per deciliter 0.1 g $K_2HPO_4$, 0.1 g $MgSO_4.7H_2O$, and 3.0 g yeast extract, of pH 6.0 was placed in 500 ml flasks and heated with steam Aspergillus sojae AJ 7002 was inoculated in the aqueous culture media and cultured at 30° C for 70 hours with shaking.

The resultant culture broth was filtered with guaze to remove mycerium, and mixed with 50 ml of acetone. Fibrous precipitates were winded on glass rod, washed with ethylalcohol and freeze-dried. It weighed 56 mg. Each protein (microbial cells or proteins) listed in Table 2 (200 mg) was suspended or dissolved in 50 ml water placed in 50 ml graduated cylinder.

The mucopolysaccharide mentioned above was dissolved in 50 ml of 0.01N HCl and a portion of the solution was added to the graduated cylinder to contain in the protein suspension 5 ppm or 10 ppm. Sedimentation rate of the microbials cells was determined by measuring the height of clear part in the cylinder. Sedimentation rate of proteins was determined by weighing filtered protein precipitates. The results are shown in Table 2.

EXAMPLE 2

An aqueous culture medium was prepared to contain, per deciliter, 0.1 g $KH_2PO_4$, 0.1 g $MgSO_4.7H_2O$, 0.2 g $(NH_4)_2SO_4$ and 2.0 g casein, adjusted to pH 6.0.

Aspergillus flavus AJ 17047 was cultured and the flocculant accumulated in the culture broth was recovered by the analogus manner as in Example 1. The mucopolysaccaride recovered weighed 73 mg.

The flocculation activity of the mucopolysaccharide was determined by the same method as in Example 1 and is shown in Table 3.

EXAMPLE 3

A half liter of waste water of fish processing (optical density at 520 nm being 0.75, being pH 6.7, being COD 1400 ppm and containing 500 ppm proteins) was added with the mucopolysaccharide shown in Example 1 to contain 20 ppm, and filtered to remove precipitates formed. Optical density of the filtrate at 520 nm was 0.15, pH was 6.7, COD was 120 ppm and proteins concentration was 8 ppm.

EXAMPLE 4

Bakers' yeast (200 g) was extracted with 1 liter of boiling water of pH 8.0 for an hour, the water solution was centrifuged and the resultant supernatant contained 14.0% residue on evaporation and was 2.8 optical density at 520 nm. The water solution was added with 10 ppm of the mucopolysaccharide shown in Example 1, and centrifuged at 1000 r.p.m. for 30 minutes, whereby the optical density was reduced to 0.1.

While, when sodiun alginate or polyacrylamine (each 10 ppm) was used in place of the mucopolysaccharide to the waste water, the optical density of the waste water was not reduced.

EXAMPLE 5

Activated sladge (200 ml) containing 3.2% residues on evapolation was added with 200, or 400 ppm of the mucopolysaccharide of Example 1 and stirred for 5 minutes, and placed in 200 ml graduated cylinder.

For the purpose of comparison, sodium alginate, polyacrylamide or ferric chloride was used as the flocculant.

The sedimentation rates are shown in Table 4.

Table 1

| Amino acid | (%) |
|---|---|
| Tryptophan | — |
| Lysine | 0.9 |
| Histidine | 0.4 |
| Ammonia | — |
| Arginine | 0.9 |
| Cysteic acid | 0.1 |
| Taurine | — |
| Aspartic acid | 1.9 |
| Threonine | 0.8 |
| Serine | 2.2 |
| Glutamic acid | 4.3 |
| Proline | 0.9 |
| Glycine | 0.8 |
| Alanine | 1.2 |
| Cystine | 0.1 |
| Valine | 2.9 |
| Methionine | 0.4 |
| Isoleucine | 1.4 |
| Leucine | 1.7 |
| Tysosine | 3.5 |
| Phenylalanine | 1.2 |
| β-Alanine | — |
| Glucosamine | — |
| γ-Aminobutylic acid | — |
| Total | 25.6 |

Table 2

| | Sedimentation rate (cm/min) | | |
|---|---|---|---|
| | The amount of flocculant | | |
| Proteins | 0 | 5 | 10ppm |
| Microbial cells | | | |
| Candida lipolytica ATCC 16618 | 0.03 | 1.8 | 3.2 |
| Saccharomyces cerevisiae ATCC 15248 | 0.01 | 1.9 | 3.3 |
| Rhodotorula glutinis ATCC 4054 | 0.04 | 2.0 | 3.1 |
| Endomycopsis burtonii ATCC 13169 | 0.05 | 1.5 | 2.6 |
| Hansenula anomala ATCC 2149 | 0.02 | 1.8 | 3.2 |
| Debaryomyces vanriji ATCC 20125 | 0.03 | 1.8 | 3.8 |
| Pichia ohmeri ATCC 9766 | 0.02 | 2.1 | 3.9 |
| Trycosporon fermentans ATCC 10675 | 0.03 | 1.3 | 2.8 |
| Brevibacterium flavum ATCC 14067 | less than 0.01 | 1.4 | 2.5 |
| Brevibacterium lacto- fermentum ATCC 13869 | less than 0.01 | 1.7 | 3.2 |
| Bacillus megatherium ATCC 6455 | less than 0.01 | 0.9 | 2.3 |
| Bacillus subtilis ATCC 6051 | less than 0.01 | 1.1 | 2.4 |
| Escherichia coli ATCC 4157 | less than 0.01 | 0.5 | 1.3 |
| Oerskovia turbata ATCC 25835 | less than 0.01 | 0.7 | 1.8 |
| Chlorella burgaris ATCC 9765 | 0.05 | 3.5 | 4.3 |
| Manaskas anka ATCC 16360 | 0.12 | 4.6 | 7.8 |
| Proteins | | | |
| milk casein | less than 0.01 | 0.3 | 1.2 |
| bovin albumin | less than 0.01 | 0.2 | 1.1 |
| soybean protein (containing 53.7% protein) | less than 0.01 | 0.3 | 1.2 |

Table 3

| | Sedimentation rate(cm/min) | | |
|---|---|---|---|
| | The amount of flocculant added | | |
| Proteins | 0 | 5 | 10ppm |
| Microbial cells | | | |
| Candida lipolytica ATCC 16618 | 0.03 | 1.9 | 3.3 |
| Saccharomyces cerevisiae ATCC 15248 | 0.02 | 2.0 | 3.4 |
| Rhodotorula glutinis ATCC 4054 | 0.03 | 2.3 | 3.2 |

Table 3-continued

| Proteins | Sedimentation rate(cm/min) The amount of flocculant added | | |
|---|---|---|---|
| | 0 | 5 | 10ppm |
| Endomycopsis burtonii ATCC 13169 | 0.04 | 1.5 | 3.0 |
| Hansenula anomala ATCC 2149 | 0.02 | 1.9 | 3.2 |
| Debaryomyces vanriji ATCC 20125 | 0.03 | 1.8 | 3.8 |
| Pichia ohmeri ATCC 9766 | 0.02 | 2.1 | 3.9 |
| Trycosporon fermentans ATCC 10675 | 0.03 | 1.3 | 3.0 |
| Brevibacterium flavum ATCC 14067 | less than 0.01 | 1.4 | 2.5 |
| Brevibacterium lacto-fermentum ATCC 13869 | less than 0.01 | 1.7 | 3.2 |
| Bacillus megatherium ATCC 6458 | less than 0.01 | 0.9 | 2.3 |
| Bacillus subtilis ATCC 6051 | less than 0.01 | 1.1 | 2.4 |
| Escherichia coli ATCC 4157 | less than 0.01 | 0.6 | 1.6 |
| Oerskovia turbata ATCC 25835 | less than 0.01 | 0.8 | 1.9 |
| Chlorella burgaris ATCC 9765 | 0.05 | 3.5 | 4.3 |
| Monaskas anka ATCC 16360 | 0.12 | 4.6 | 7.8 |
| Proteins | | | |
| milk casein | less than 0.01 | 0.5 | 1.2 |
| bovin albumin | less than 0.01 | 0.6 | 1.3 |
| soybean protein (containing 53.7% protein) | less than 0.01 | 0.5 | 1.3 |

Table 4

| Flocculant | Amount used (ppm) | Sedimentation rate (cm/hr) |
|---|---|---|
| The mucopolysaccharide of this invention | 200 | 2.3 |
| | 400 | 4.2 |
| Polyacrylamide | 400 | 1.2 |
| FeCl$_3$ | 4000 | 3.2 |
| none | — | 1.2 |

What is claimed is:

1. A mucopolysaccharide having flocculating activity for protein which is inactivated by treatment with a protease or with periodic acid characterized by the following chemical and physical properties:
   1. The ultraviolet spectrum of FIG. 1;
   2. The infrared spectrum of FIG. 2;
   3. Containing carbon, hydrogen, oxygen and nitrogen;
   4. Containing the following moieties: glutamic acid, tyrosine, valine, serine, leucine, aspartic acid, isoleucine, alanine, phenylalanine, proline, galactosamine, glucosamine, and 2-ketogluconic acid;
   5. Having a molecular weight by the gel filtration method greater than $2 \times 10^5$;
   6. Exhibiting a positive Lowry reaction and a negative iodo starch reaction;
   7. Being slightly soluble in water and soluble in dilute aqueous acid or alkali; and
   8. Exhibiting a viscosity of 400 C.P. in 1.0% solution in ammonium chloride as measured with a B-type viscometer at 22° C.

2. A method for producing a mucopolysaccharide of claim 1 which comprises aerobically culturing a microorganism of the genus Aspergillus and being capable of producing said mucopolysaccharide in an aqueous nutrient medium at a pH of from 3 to 8 at from 20° C to 40° C until a substantial amount of said mucopolysaccharide accumulates in the culture medium and recovering the accumulated mucopolysaccharide.

* * * * *